United States Patent
Kolbe et al.

(10) Patent No.: US 9,533,963 B2
(45) Date of Patent: Jan. 3, 2017

(54) ALKYLAMIDOTHIAZOLES, COSMETIC OR DERMATOLOGICAL PREPARATIONS CONTAINING SAID ALKYLAMIDOTHIAZOLES, AND USE THEREOF TO COMBAT OR PREVENT UNDESIRED PIGMENTATION OF THE SKIN

(71) Applicant: BEIERSDORF AG, Hamburg (DE)

(72) Inventors: Ludger Kolbe, Dohren (DE); Cathrin Scherner, Hamburg (DE); Sabrina Breitkreutz, Hamburg (DE); Michael Woehrmann, Norderstedt (DE); Tobias Mann, Hamburg (DE); Wolfram Gerwat, Hamburg (DE); Torsten Schlaeger, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 162 days.

(21) Appl. No.: 14/126,078

(22) PCT Filed: Sep. 18, 2012

(86) PCT No.: PCT/EP2012/068362
§ 371 (c)(1),
(2) Date: Dec. 13, 2013

(87) PCT Pub. No.: WO2013/041526
PCT Pub. Date: Mar. 28, 2013

(65) Prior Publication Data
US 2014/0121250 A1    May 1, 2014

(30) Foreign Application Priority Data
Sep. 23, 2011   (DE) .......................... 10 2011 083 259

(51) Int. Cl.
| | | |
|---|---|---|
| C07D 277/46 | (2006.01) | |
| C07D 277/48 | (2006.01) | |
| A61K 8/49 | (2006.01) | |
| A61Q 19/00 | (2006.01) | |

(52) U.S. Cl.
CPC ............ C07D 277/46 (2013.01); A61K 8/49 (2013.01); A61Q 19/00 (2013.01); C07D 277/48 (2013.01)

(58) Field of Classification Search
CPC .................................................. C07D 277/44
See application file for complete search history.

(56) References Cited

U.S. PATENT DOCUMENTS

| | | | |
|---|---|---|---|
| 8,426,435 B2 | 4/2013 | Hanyu et al. | |
| 2004/0224992 A1* | 11/2004 | Cywin | C07C 235/38 514/357 |
| 2007/0042997 A1 | 2/2007 | Itai et al. | |
| 2010/0316584 A1 | 12/2010 | Hanyu et al. | |
| 2010/0324096 A1 | 12/2010 | Hanyu et al. | |
| 2011/0003817 A1 | 1/2011 | Hanyu et al. | |
| 2011/0003838 A1 | 1/2011 | Hanyu et al. | |
| 2012/0134944 A1 | 5/2012 | Hanyu et al. | |
| 2013/0039870 A1 | 2/2013 | Kolbe et al. | |
| 2013/0045173 A1 | 2/2013 | Hanyu et al. | |

FOREIGN PATENT DOCUMENTS

| | | |
|---|---|---|
| EP | 1649852 A1 | 4/2006 |
| EP | 2251001 A1 | 11/2010 |
| WO | 2009099195 A1 | 8/2009 |
| WO | 2011117034 A2 | 9/2011 |

OTHER PUBLICATIONS

Registry database print-out Registry of May 30, 2012.
Germanas et al: "Discovery of small-molecule inhibitors of tyrosinase", Bioorganic & Medicinal Chemistry Letters, Pergamon, Elsevier Science, GB, vol. 17, No. 24, Oct. 12, 2007.
Morales-Bonilla, Pedro et al: "Preparation, antimicrobial activity, and toxicity of 2-amino-4-arylthiazole derivates", Heteroatom Chemistry, vol. 17, No. 4, 2006, pp. 254-260.
Chemical Abstracts Services, Columbus, Ohio, US; 2007, Chhabria, M.T. et al: "Synthesis and antifungal activity of some novel N-[4-(4-substituted phenyl)-1, 3-thiazol-2-yl]-2-(1H-1, 2, 4-triazol-1-yl) propionamides" & Chhabria, M.T. et al: "Synthesis and antifungal activity of some novel N-[4-(4-substituted phenyl)-1, 3-thiazol-2-yl]-2(1H-1, 2, 4-triazol-1-yl) propionamides" Acta Ciencia Indica, Chemistry, 33(1), 101-103, 2007.

(Continued)

Primary Examiner — Michael Barker
Assistant Examiner — Karen Cheng
(74) Attorney, Agent, or Firm — Abel Law Group, LLP

(57) ABSTRACT

Alkylamidothiazoles of general formula (I), wherein R1=—C1-C24 alkyl (linear and branched), —C1-C24 alkenyl (linear and branched), —C1-C8 cycloalkyl, —C1-C8 cycloalkyl-alkylhydroxy, —C1-C24 alkylhydroxy (linear and branched), —C1-C24 alkylamine (linear and branched), —C1-C24 alkylaryl (linear and branched), —C1-C24 alkylaryl-alkyl-hydroxy (linear and branched), —C1-C24 alkylheteroaryl (linear and branched), —C1-C24-alkyl-O—C1-C24-alkyl (linear and branched), —C1-C24 alkyl morpholino, —C1-C24 alkyl piperidino, —C1-C24 alkyl piperazino, —C1-C24 alkyl-piperazino-N-alkyl, as well as cosmetic or dermatological preparations having an effective content of one or more alkylamidothiazoles, as well as the use thereof for the cosmetic or dermatological treatment and/or prophylaxis of undesired skin pigmentation.

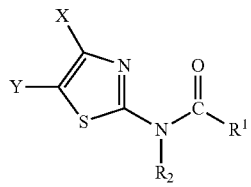

20 Claims, No Drawings

(56) References Cited

OTHER PUBLICATIONS

Database CA [Online] Chemical Abstracts Service, Columbus, Ohio, US; 1998, Shrivastava, A. K. et al: "Syntheses of some 2-amino-4-(aryl/substituted aryl)thiazoles and their thiazolylamides as potential antifungal agents. II", XP002687088, found in STN Database accession No. 1998:209541 & Shrivastava, A. K. et al: "Syntheses of some 2-amino-4-(aryl/substituted aryl)thiazoles and their thiazolylamides as potential antifungal agents. II", Journal of the Institution of Chemists (India) , 69(6), 167-168 CODEN: JOICA7; ISSN: 0020-3254.
Database CA [Online] Chemical Abstracts Service, Columbus, Ohio, US; 2010, Pattan, S. R. et al: "Synthesis and evaluation of some new phenylthiazole derivatives for their anti-microbial activities", XP002687089, found in STN Database accession No. 2010:919247 & Pattan, S. R. et al: "Synthesis and evaluation of some new phenylthiazole derivatives for their anti-microbial activities", Asian Journal of Research in Chemistry , 2(3), 292-296 CODEN: AJRCBL; ISSN: 0974-4150 URL: http://www.ajrconline.org/pdf/ajrc_2_3_2009.
Agrawal R K et al: "Synthesis of some basic N-4-arylthiazolyl and n-4(substituted) arylthiazolylbutyramides as potential local anaesthetics", Journal of the Indian Chemical Society, The Indian Chemical Society, Calcutta; IN, vol. 58, Jan. 1, 1981 (Jan. 1, 1981), pp. 787-788, XP009086881, ISSN: 0019-4522.

* cited by examiner

ALKYLAMIDOTHIAZOLES, COSMETIC OR DERMATOLOGICAL PREPARATIONS CONTAINING SAID ALKYLAMIDOTHIAZOLES, AND USE THEREOF TO COMBAT OR PREVENT UNDESIRED PIGMENTATION OF THE SKIN

The present invention relates to new alkylamidothiazoles, to cosmetic or dermatological preparations with a content of one or more such alkylamidothiazoles and to the use of such alkylamidothiazoles or preparations comprising such alkylamidothiazoles for combating or preventing undesired pigmentation of the skin.

Melanocytes are responsible for the pigmenting of the skin; these are found in the lowest layer of the epidermis, the Stratum basale, alongside the basal cells as pigment-forming cells which, depending on the skin type, occur either individually or in clusters of varying size.

Melanocytes contain, as characteristic cell organelles, melanosomes, in which the melanin is formed. Inter alia, upon stimulation by UV radiation, melanin is formed to a greater extent. This is transported via the living layers of the epidermis (keratinocytes) ultimately into the horny layer (corneocytes) and brings about a more or less pronounced brownish to brown-black skin color.

Melanin is formed as the end stage of an oxidative process in which tyrosine is converted, under the co-action of the enzyme tyrosinase, via several intermediates, to the brown to brown-black eumelanins (DHICA and DHI melanin), or, with the participation of sulfur-containing compounds, to the reddish pheomelanin. DHICA and DHI melanin are formed via the common intermediates dopaquinone and dopachrome. The latter, sometimes with the participation of further enzymes, is converted either to indol-5,6-quinonecarboxylic acid or into indol-5,6-quinone, from which the two specified eumelanins are formed.

The formation of pheomelanin proceeds inter alia via the intermediates dopaquinone and cysteinyldopa. The expression of the melanin-synthesizing enzymes is controlled by a specific transcription factor (microphthalmia-associated transcription factor, MITF). Besides the described enzymatic processes of the melanin synthesis, further proteins are also of importance for the melanogenesis in the melanosomes. An important role here appears to be attributed to the so-called p-protein, although the exact function is still unclear.

As well as the above-described process of the melanin synthesis in the melanocytes, the transfer of the melanosomes, their stay in the epidermis and also their degradation and the degradation of the melanin are also of decisive importance for the pigmenting of the skin. It was shown that the PAR-2 receptor is important for the transport of the melanosomes from the melanocytes into the keratinocytes (M. Seiberg et al., 2000, J. Cell. Sci., 113:3093-101).

In addition, size and shape of the melanosomes have an influence on their light-scattering properties and thus the color appearance of the skin. For example, in black Africans there are more large spheroidal individual melanosomes, whereas in Caucasians, smaller melanosomes occurring in groups are to be found.

Problems with hyperpigmentation of the skin have a wide variety of causes and/or are accompanied phenomena of many biological processes, e.g. UV radiation (e.g. freckles, *Ephelides*), genetic disposition, incorrect pigmentation of the skin during wound healing or scarring (post-inflammatory hyperpigmentation) or skin aging (e.g. *Lentigines seniles*).

After inflammatory reactions, the pigmentation system of the skin reacts with sometimes opposite reactions. This can lead either to post-inflammatory hyperpigmentations or hypopigmentations. Post-inflammatory hypomelanoses often arise inter alia in conjunction with atopy, Lupus erythematosus and psoriasis. The different reaction forms of the pigmentation system of the human skin as a result of inflammatory phenomena are understood only very incompletely.

Problems with post-inflammatory hyperpigmentation often occur in darker skin types. Particularly in colored males, the problem of *Pseudofollikulitis barbae* is known, which is associated with cosmetically undesired incorrect pigmentation and/or leads to this. Forms of melasma, which occur in particular in women of Asiatic origin on the face and on the décolletage area, and also various forms of irregular pigmentation of the skin are also types of post-inflammatory hyperpigmentations. In addition, dark circles around the eyes are also considered to be a form of post-inflammatory hyperpigmentations, the underlying inflammation in most cases proceeding without clinical manifestations.

In many cases, post-inflammatory incorrect pigmentation of this type is increased further by the action of sunlight (UV light) without resulting in a UV-induced inflammation (sunburn).

Active ingredients and preparations are known which counteract skin pigmentation. In practical use these are essentially preparations based on hydroquinone, although, on the one hand, these only exhibit their effect after application for several weeks, and, on the other hand, their excessively long application is unacceptable for toxicological reasons. Albert Kligman et al. has developed a so-called "triformula" which constitutes a combination of 0.1% tretinoin, 5.0% hydroquinone, 0.1% dexamethasone (A. Kligman, 1975, Arch. Dermatol., 111:40-48). However, this formulation too is highly disputed on account of possible irreversible changes in the pigmentation system of the skin.

In addition, skin-peeling methods (chemical and mechanical "peels") are used, although these often lead to inflammatory reactions and, on account of post-inflammatory hyperpigmentations which may subsequently arise, can even lead to greater pigmentation instead of reduced pigmentation. All of these customary methods, which are also used for treating post-inflammatory hyperpigmentations, are characterized by distinct side effects.

Furthermore, various other substances are known for which a skin-lightening effectiveness is described. Mention is to be made here inter alia of hexadecene-1,16-dicarboxylic acid, kojic acid and derivatives, arbutin, ascorbic acid and derivatives, flavonoids, ellagic acid and derivatives, tranexamic acid and various resorcinol derivatives, such as e.g. 4-n-butylresorcinol, 4-n-hexylresorcinol and 4-(1-phenylethyl)benzene-1,3-diol.

J. M. Ready describes in a publication (Bioorganic & Medicinal Chemistry Letter 17 (2007) 6871-6875 the effect of inter alia substituted thiazole derivatives for the inhibition of mushroom tyrosinase.

The patent application from Shiseido (WO 2009/099195) describes substituted thiazolamines and hydrothiazolamines for lightening skin.

The substances described in the aforementioned prior art show a moderate effectiveness and/or a poor galenical stability.

Rings around the eyes can likewise be formed as a result of a pigmentation disorder, with them in addition also appearing as a reaction to general stress, such as e.g. too little sleep or simply as a result of overexerting the eyes. In younger people, the symptoms disappear again after an adequate nighttime rest, but, over prolonged periods, the condition can become chronic and very troublesome for those affected. There is also a lack of sufficiently promising active ingredients and treatment options to combat such skin phenomena.

It was therefore an aim of the invention below to provide a remedy for the disadvantageous prior art.

The solution to the problems underlying the invention consists in alkylamidothiazoles of the general formula

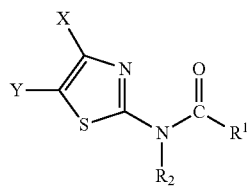

in which
$R^1$, $R^2$, X and Y can be different, partly identical or completely identical and, independently of one another, can mean:
$R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl,
$R_2$=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-hydroxyalkyl (linear and branched), —$C_1$-$C_{24}$-alkylaryl (linear and branched), —$C_1$-$C_{24}$-alkylheteroaryl (linear and branched),
X=—H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl (optionally mono- or polysubstituted with —OH, —F, —Cl, —Br, —I, —OMe, —$NH_2$, —CN), —$C_1$-$C_{24}$-heteroaryl (optionally mono- or polysubstituted with —OH, —F, —Cl, —Br, —I, —OMe, —$NH_2$, —CN), —$C_1$-$C_{24}$-alkylaryl (linear and branched), —$C_1$-$C_{24}$-alkylheteroaryl (linear and branched), -aryl (optionally mono- or polysubstituted with —OH, —F, —Cl, —Br, —I, —OMe, —$NH_2$, —CN), -phenyl, -2,4-dihydroxyphenyl, -2,3-dihydroxyphenyl, -2,4-dimethoxyphenyl, -2,3-dimethoxyphenyl,
Y=H, —$C_1$-$C_{24}$-alkyl (linear and branched), —$C_1$-$C_{24}$-alkenyl (linear and branched), —$C_1$-$C_8$-cycloalkyl, —$C_1$-$C_{24}$-aryl, —$C_1$-$C_{24}$-heteroaryl, —$C_1$-$C_{24}$-alkylaryl (linear and branched), —$C_1$-$C_{24}$-alkylheteroaryl (linear and branched), -aryl, -phenyl, -2,4-dihydroxyphenyl, -2,3-dihydroxyphenyl, -2,4-dimethoxyphenyl, -2,3-dimethoxyphenyl, —COO-alkyl, —COO-alkenyl, —COO-cycloalkyl, —COO-aryl, —COO-heteroaryl,
and X, Y can optionally also mean=condensed aromatic, where X and Y can form with one another aromatic or aliphatic homo- or heterocyclic ring systems with up to n ring-forming atoms, and where the number n can assume values from 5 to 8, and the respective ring systems can in turn be substituted with up to n−1 alkyl groups, hydroxyl groups, carboxyl groups, amino groups, nitrile functions, sulfur-containing substituents, ester groups and/or ether groups.

Said thiazoles can either be in the form of the free base or the salt: e.g. fluoride, chloride, bromide, iodide, sulfate, carbonate, ascorbate, acetate or phosphate. In particular in the form of halogen salts, such as e.g. chloride and bromide.

Furthermore, there is an advantageous realization of the present invention in cosmetic or dermatological preparations with an effective content of one or more aforementioned alkylamidothiazoles.

Also in accordance with the invention is the use of the aforementioned alkylamidothiazoles for the treatment and/or prophylaxis of undesired skin pigmentation.

Here, treatment and/or prophylaxis of undesired skin pigmentation can be both in the cosmetic sphere and in the pharmaceutical sphere.

In this connection, the pharmaceutical (or dermatological) treatment is primarily understood for diseased skin conditions, whereas the cosmetic treatment and/or prophylaxis of undesired skin pigmentation primarily relates to healthy skin.

Advantageously, X is selected from the group of substituted phenyls, in which case the substituents (Z) can be selected from the group —H, —OH, —F, —Cl, —Br, —I, —OMe, —$NH_2$, —CN, acetyl and can be identical or different.

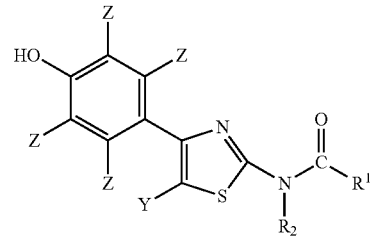

Particularly advantageously, X is selected from the group of phenyl groups substituted with one or more hydroxy groups, in which case the substituent (Z) can be selected from the group —H, —OH, —F, —Cl, —Br, —I, —OMe, —$NH_2$, —CN, acetyl, and preference is given to the following generic structure in which Y, $R^1$ and $R^2$ can have the properties defined above.

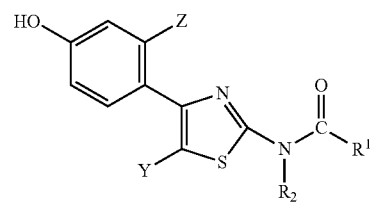

Particularly advantageous compounds are those in which

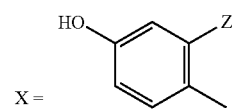

Y=H $R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$ alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$-alky-morpholino, —$C_1$-$C_{24}$ alky-piperidino, —$C_1$-$C_{24}$ alky-piperazino, —$C_1$-$C_{24}$ alky-piperazino-N-alkyl, $R_2$=H, —$C_1$-$C_{24}$-alkyl (linear and branched), Z=—H, —OH, —F, —Cl, —Br, —I, —OMe, —$NH_2$, —CN, acetyl.

Particular preference is given to those compounds in which

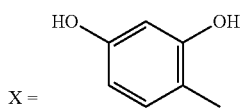

Y=H $R_1$=—$C_1$-$C_{24}$-alkyl (linear and branched), —$C_1$-$C_{24}$-alkenyl (linear and branched), —$C_1$-$C_8$-cycloalkyl, —$C_1$-$C_8$-cycloalkyl-alkylhydroxy, —$C_1$-$C_{24}$-alkylhydroxy (linear and branched), —$C_1$-$C_{24}$ alkylamine (linear and branched), —$C_1$-$C_{24}$-alkylaryl (linear and branched), —$C_1$-$C_{24}$-alkylaryl-alkyl-hydroxy (linear and branched), —$C_1$-$C_{24}$-alkylheteroaryl (linear and branched), —$C_1$-$C_{24}$-alkyl-O—$C_1$-$C_{24}$-alkyl (linear and branched), —$C_1$-$C_{24}$ alky-morpholino, —$C_1$-$C_{24}$ alky-piperidino, —$C_1$-$C_{24}$ alky-piperazino, —$C_1$-$C_{24}$ alky-piperazino-N-alkyl, $R_2$=H.

The compounds

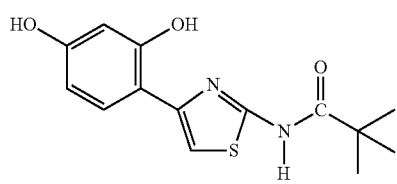

N-(4-(2,4-dihydroxyphenyl)thiazol-2-yl)pivalamide

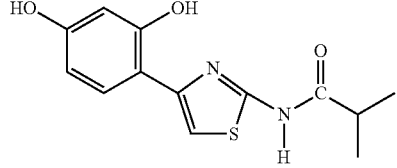

N-(4-(2,4-dihydroxyphenyl)thiazol-2-yl)isobutyramide

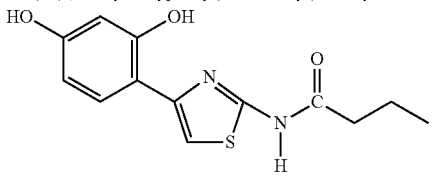

N-(4-(2,4-dihydroxyphenyl)thiazol-2-yl)butyramide

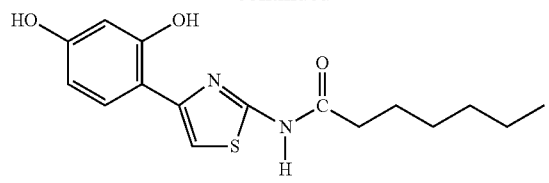

N-(4-(2,4-dihydroxyphenyl)thiazol-2-yl)heptanamide

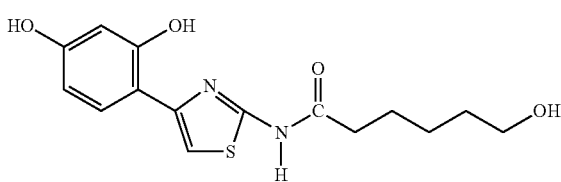

N-(4-(2,4-dihydroxyphenyl)thiazol-2-yl)-6-hydroxyhexanamide

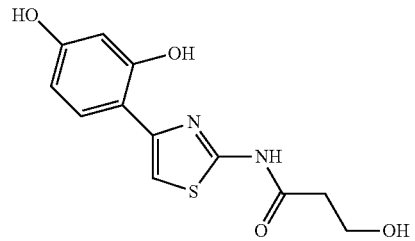

N-(4-(2,4-dihydroxyphenyl)thiazol-2-yl)-3-hydroxypropanamide

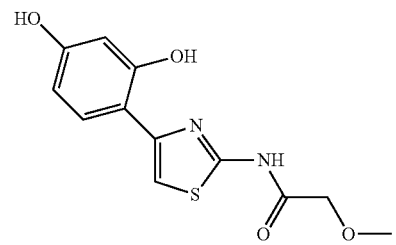

N-(4-(2,4-dihydroxyphenyl)thiazol-2-yl)-2-methoxyacetamide

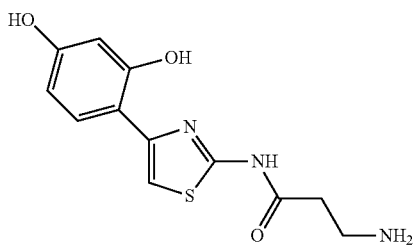

3-amino-N-(4-(2,4-dihydroxyphenyl)thiazol-2-yl)propanamide

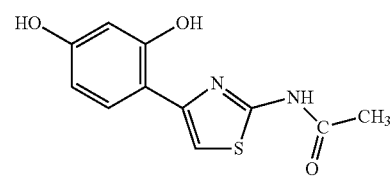

N-(4-(2,4-dihydroxyphenyl)thiazol-2-yl)acetamide

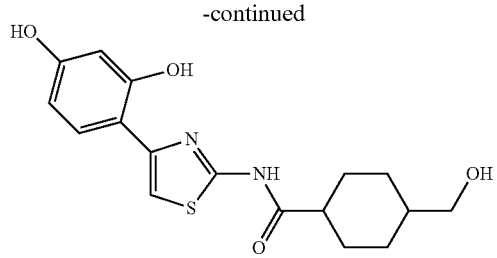

N-(4-(2,4-dihydroxyphenyl)thiazol-2-yl)-4-(hydroxymethyl)cyclohexanecarboxamide

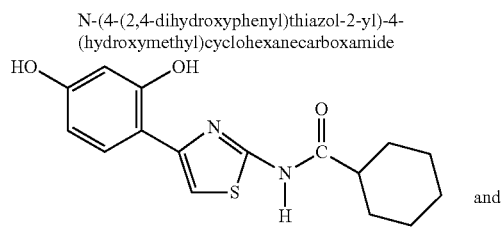

and

N-(4-(2,4-dihydroxyphenyl)thiazol-2-yl)cyclohexanecarboxamide

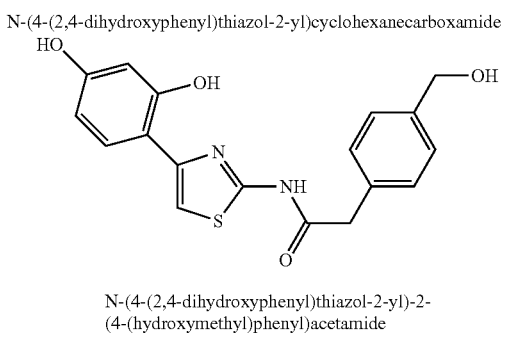

N-(4-(2,4-dihydroxyphenyl)thiazol-2-yl)-2-(4-(hydroxymethyl)phenyl)acetamide are preferred according to the invention.

Surprisingly, it was able to be shown that the alkylamidothiazoles according to the invention have a higher galenical stability and/or increased effectiveness compared to the corresponding alkylaminothiazoles.

See Table 1 and Table 2.

Method Description of the Stability Investigations:

For the purposes of incorporation into the formulations, the amines and amides were dissolved in butylene glycol—optionally with heating—and added to the emulsion before the first homogenization at ca. 65° C. All of the active ingredients were incorporated in a concentration of 0.1% in the experimental batches.

The emulsion was poured into 20 ml glass vials for the storage tests and stored under various standard conditions (room temperature, light and 40° C.).

For the stability investigations, the stored samples were analyzed after 14 days.

Analysis/Recovery:

The samples to be measured were extracted in a methanol/water mixture [70:30] and determined by means of HPLC-DAD. The determination was carried out by means of external standard calibration [reference section]. The evaluation was carried out at 296 nm.

Instrument:

HPLC: Agilent 1100

Column: Phenomenex Synergi MAX-RP, 50×2 mm i.d. [2.5 μm]

Solvent: gradient acetonitrile/water with 0.1% phosphoric acid

Flow rate: 0.3 ml/min

| Gradient: | | |
|---|---|---|
| Time [min] | H2O [%] 0.1% H3PO4 | MeCN [%] |
| 0.0 | 90.0 | 10.0 |
| 10.0 | 10.0 | 90.0 |
| 12.0 | 10.0 | 90.0 |
| 13.0 | 90.0 | 10.0 |
| 20.0 | 90.0 | 10.0 |

Injection volume: 3 μl

The raw materials used in each case served as reference.

TABLE 1

| Test sample | Recovery [%] | |
|---|---|---|
| Formula 1 - with N-(4-(2,4-dihydroxyphenyl)thiazol-2-yl)isobutyramide | 100 | Amide |
| Formula 2 - with 4-(2-isopropylamino)thiazol-4-yl)benzene-1,3-diol | 70 | Amine |
| Formula 3 - with 4-(2-(tert-butylamino)thiazol-4-yl)benzene-1,3-diol | 93 | Amine |
| Formula 4 - with N-(4-(2,4-dihydroxyphenyl)thiazol-2-yl)pivalamide | 100 | Amide |
| Formula 5 - with N-(4-(2,4-dihydroxyphenyl)thiazol-2-yl)butyramide | 100 | Amide |
| Formula 6 - with 4-(2-propylamino)thiazol-4-yl)benzene-1,3-diol | 84 | Amine |
| Formula 7 - with N-(4-(2,4-dihydroxyphenyl)thiazol-2-yl)cyclohexanecarboxamide | 99 | Amide |
| Formula 8 - with 4-(2-(cyclohexylamino)thiazol-4-yl)benzene-1,3-diol | 90 | Amine |
| Formula 9 - with N-(4-(2,4-dihydroxyphenyl)thiazol-2-yl)heptanamide | 100 | Amide |
| Formula 10 - with 4-(2-(hexylamino)thiazol-4-yl)benzene-1,3-diol | 86 | Amine |

Method Description of the Effectiveness Investigations:

The effectiveness of the thiazoles was demonstrated using an enzyme test in which conversion of L-DOPA to L-dopaquinone by a human tyrosinase was measured. In this literature-known method (Winder, A. J. and Harris, H., New assays for the tyrosine hydroxylase and dopa oxidase activities of tyrosinase. Eur. J. Biochem. (1991), 198, 317-26), the reaction product L-dopaquinone is reacted with MBTH (3-methyl-2-benzothiazoline hydrazone) to give a pink-colored substance, the increase of which is measured over the time by absorption at 490 nm. Table 1 shows by way of example the effectiveness data for some of the claimed substances. It can be concluded from this that the substances according to the invention are extremely effective pigmentation-inhibiting substances.

TABLE 2

Inhibition of the tyrosinase activity by thiazoles

| Substance | Inhibition (% of the control) | Concentration |
|---|---|---|
| N-(4-(2,4-Dihydroxyphenyl)thiazol-2-yl)isobutyramide | 94 | 10 μg/ml |
| 4-(2-Isopropylamino)thiazol-4-yl)benzene-1,3-diol | 91 | 10 μg/ml |
| N-(4-(2,4-Dihydroxyphenyl)thiazol-2-yl)heptanamide | 66 | 10 μg/ml |
| 4-(2-(Hexylamino)thiazol-4-yl)benzene-1,3-diol | 41 | 10 μg/ml |
| 4-(2-(tert-Butylamino)thiazol-4-yl)benzene-1,3-diol | 62 | 10 μg/ml |

TABLE 2-continued

Inhibition of the tyrosinase activity by thiazoles

| Substance | Inhibition (% of the control) | Concentration |
|---|---|---|
| N-(4-(2,4-Dihydroxyphenyl)thiazol-2-yl)pivalamide | 96 | 10 μg/ml |
| N-(4-(2,4-Dihydroxyphenyl)thiazol-2-yl)butyramide | 95 | 10 μg/ml |
| 4-(2-(Propylamino)thiazol-4-yl)benzene-1,3-diol | 88 | 10 μg/ml |
| N-(4-(2,4-Dihydroxyphenyl)thiazol-2-yl)cyclohexanecarboxamide | 92 | 10 μg/ml |
| 4-(2-(Cyclohexylamino)thiazol-4-yl)benzene-1,3-diol | 70 | 10 μg/ml |
| N-(4-(2,4-Dihydroxyphenyl)thiazol-2-yl)-4-(hydroxymethyl)cyclohexanecarboxamide | 94 | 10 μg/ml |
| 4-(2-((4-(Hydroxymethyl)phenyl)amino)thiazol-4-yl)benzene-1,3-diol | 93 | 10 μg/ml |
| N-(4-(2,4-Dihydroxyphenyl)thiazol-2-yl)-2-(4-(hydroxymethyl)phenyl)acetamide | 88 | 10 μg/ml |

Synthesis Procedures of Alkylamidothiazoles Selected by Way of Example

2-Bromo-2',4'-bismethoxycarbonyloxyacetophenone

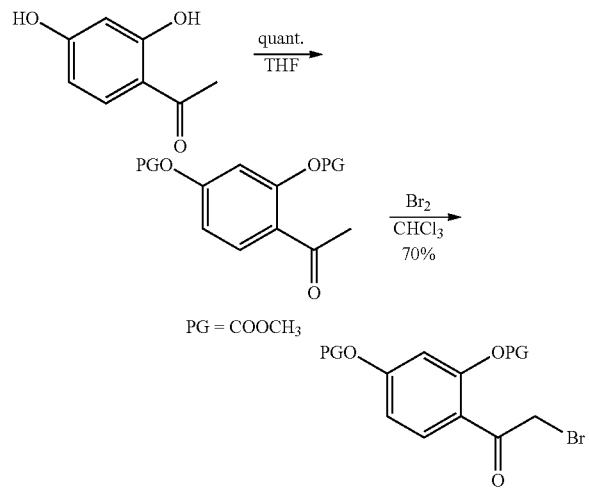

Mitchell, David; Doecke, Christopher W.; Hay, Lynne A.; Koenig, Thomas M.; Wirth, David D. Tetrahedron Letters, 1995

A solution of 60 g (369 mmol) of 2,4-dihydroxyacetophenone and 186 ml of triethylamine in 900 ml of tetrahydrofuran was cooled to 0° C., and 93 ml of methyl chloroformate in 400 ml of tetrahydrofuran was slowly added dropwise. A white precipitate is formed. After stirring for 3 hours at room temperature, the reaction is complete (TLC control). The precipitate was filtered off with suction and washed with copious amounts of tetrahydrofuran. The filtrate was evaporated to dryness on a rotary evaporator, taken up in ethyl acetate, washed with 1N HCl and NaCl solution (sat.) and dried over magnesium sulfate, filtered from the magnesium sulfate, and the ethyl acetate was concentrated on a rotary evaporator. This gave 105 g of 2,4-bismethoxycarbonyloxyacetophenone. $^1$H NMR (DMSO-D$_6$): 8.05 (d, 1H), 7.38 (d, 1H), 7.36 (s, 1H), 3.86 (d, 6H). The product was used without further purification. 63 g (392 mmol) of bromine in 450 ml of chloroform were added dropwise to the solution of 105 g of 2,4-bismethoxycarbonyloxyacetophenone in chloroform (1000 ml) over the course of 3 h. The reaction was then stirred for a further 15 min at room temperature. The solvent was evaporated on a rotary evaporator. The residue was stirred in ethyl acetate/n-hexane, and the resulting precipitate was filtered off with suction. Recrystallization from ethyl acetate/n-hexane produced 100 g of 2-bromo-2',4'-bismethoxycarbonyloxyacetophenone. $^1$H NMR (DMSO-D$_6$): 8.11 (d, 1H), 7.42 (m, 2H), 4.87 (s, 2H), 3.87 (s, 3H), 3.85 (s, 3H) ppm; m.p. 73-74° C.

N-(4-(2,4-Dihydroxyphenyl)thiazol-2-yl)pivalamide

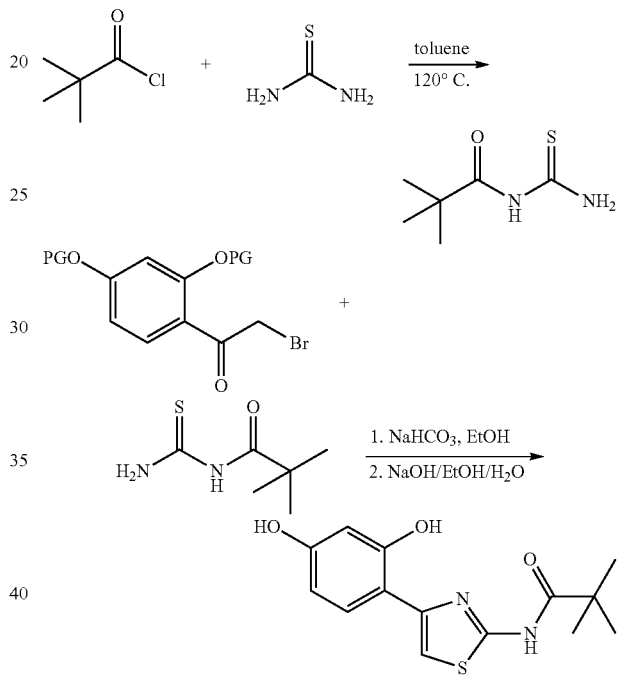

126 g (1.66 mmol) of thiourea were introduced into toluene (1000 ml), and 100 g (829 mmol) of pivaloyl chloride were added dropwise. The reaction solution was boiled under reflux for 3 hours, during which two phases formed. The upper phase was decanted off and cooled. The precipitated colorless needles were filtered off with suction and washed with cyclohexane and dried in vacuo. Yield: 64 g. $^1$H NMR (DMSO-D$_6$): 10.27 (s, 1H), 9.74 (s, 1H), 9.40 (s, 1H), 1.19 (s, 9H) ppm.

107.7 g (310 mmol) of 2-bromo-2',4'-bismethoxycarbonyloxyacetophenone were boiled with 49.7 g (13.6 mmol) of N-pivaloylthiourea and 39.2 g (466 mmol) of NaHCO$_3$ in 1.2 l of ethanol under reflux for 0.5 h. The reaction solution was cooled and admixed with 50.6 g (1.27 mol) of NaOH in 250 ml of water. After stirring for 30 min at room temperature, the reaction solution was taken up with 300 ml of water and neutralized with 2N HCl. The resulting precipitate was filtered off and recrystallized from ethanol/water. 80 g of thiazole were obtained. $^1$H NMR (DMSO-D$_6$): 11.77 (bs, 1H), 11.02 (bs, 1H), 9.47 (bs, 2H), 7.65 (d, 1H), 7.39 (s, 1H), 6.30 (s, 1H), 6.28 (d, 1H), 1.27 (s, 9H) ppm; m.p. 257-259° C.

N-(4-(2,4-Dihydroxyphenyl)thiazol-2-yl)isobutyramide

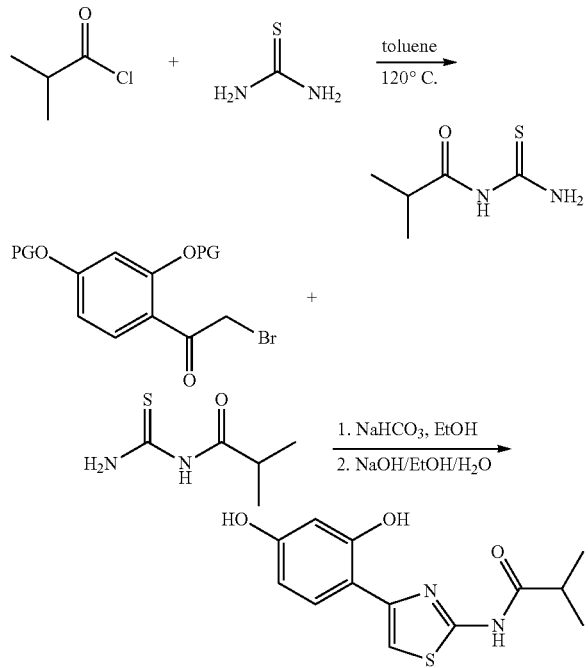

114 g (1.5 mol) of thiourea were introduced into toluene (800 ml), and 80 g (0.75 mol) of isobutyryl chloride were added dropwise. The reaction solution was boiled under reflux for 3 hours, during which two phases formed. The upper phase was decanted off and cooled. The precipitated white crystals were filtered off with suction and washed with toluene and dried in vacuo. Yield: 62 g. $^1$H NMR (DMSO-D$_6$): 11.03 (bs, 1H), 9.66 (bs, 1H), 9.35 (bs, 1H), 2.72 (m, 1H), 1.03 (2, 6H) ppm.

89 g (260 mmol) of 2-bromo-2',4'-bismethoxycarbonyloxyacetophenone were boiled under reflux with 37.5 g (260 mmol) of N-isobutyrylthiourea and 32 g (380 mmol) of NaHCO$_3$ in 1000 ml of ethanol for 0.5 h. The reaction solution was cooled and admixed with 41 g (0.93 mol) of NaOH in 250 ml of water. After stirring for 30 min at room temperature, the reaction solution was taken up with 300 ml of water and adjusted to pH=3 with 2N HCl. The resulting precipitate was filtered off and recrystallized from ethanol/water. 56 g of thiazole were obtained. $^1$H NMR (DMSO-D$_6$): 12.16 (bs, 1H), 10.88 (bs, 1H), 9.47 (bs, 1H), 7.65 (m, 1H), 7.41 (s, 1H), 6.32 (m, 2H), 2.75 (m, 1H), 1.14 (d, 6H) ppm; m.p. 243-245° C.

N-(4-(2,4-Dihydroxyphenyl)thiazol-2-yl)butyramide

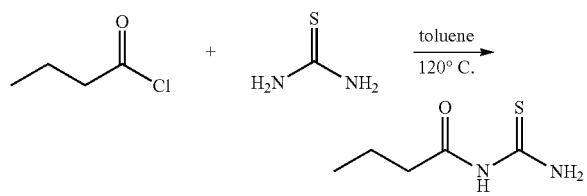

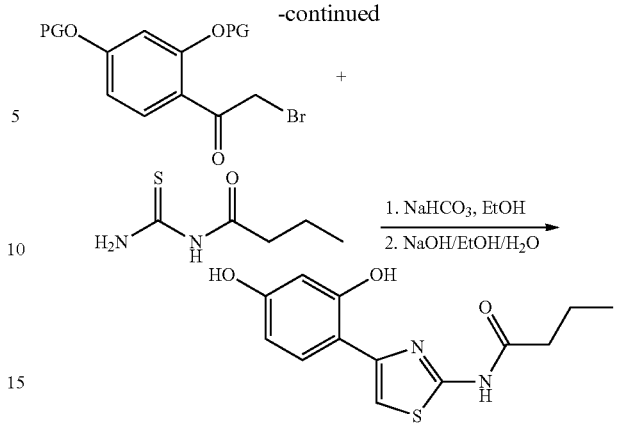

143 g (1.88 mol) of thiourea were introduced into toluene (1000 ml), and 100 g (0.93 mol) of n-butyryl chloride were added dropwise. The reaction solution was boiled under reflux for 3 hours, during which two phases formed. The upper phase was decanted off and cooled. The precipitated slightly yellowish crystals were filtered off with suction and washed with toluene and dried in vacuo. Yield: 88 g. $^1$H NMR (DMSO-D$_6$): 11.03 (bs, 1H), 9.65 (bs, 1H), 9.33 (bs, 1H), 2.33 (t, 2H), 1.53 (m, 2H), 0.86 (t, 3H) ppm; m.p. 115-188° C.

92 g (265 mmol) of 2-bromo-2',4'-bismethoxycarbonyloxyacetophenone were boiled under reflux with 38.75 g (265 mmol) of N-butyrylthiourea and 34 g (397 mmol) of NaHCO$_3$ in 900 ml of ethanol for 0.5 h. The reaction solution was cooled and admixed with 37 g (0.93 mol) of NaOH in 300 ml of water. After stirring for 30 min at room temperature, the reaction solution was taken up with 300 ml of water and neutralized with 2N HCl. The resulting precipitate was filtered off and recrystallized from ethanol/water. 67 g of thiazole were obtained. $^1$H NMR (DMSO-D$_6$): 12.18 (bs, 1H), 10.89 (bs, 1H), 9.48 (bs, 1H), 7.65 (1 arom. H), 7.40 (s, 1H), 6.31 (2 arom. H), 2.43 (t, 2H), 1.64 (m, 2H), 0.91 (t, 3H) ppm; m.p. 227-229° C.

N-(4-(2,4-Dihydroxyphenyl)thiazol-2-yl)acetamide

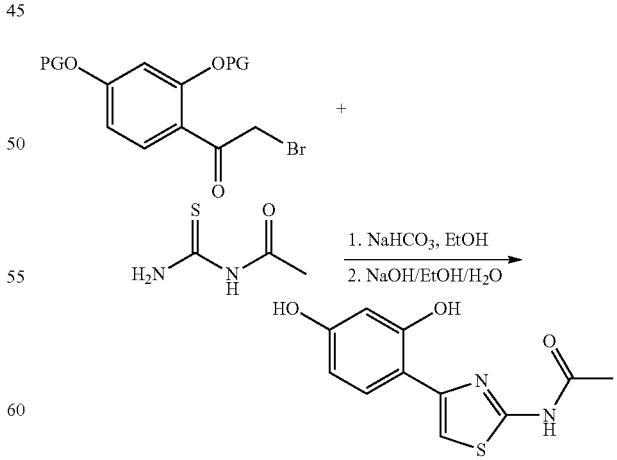

4.71 g (13.6 mmol) of 2-bromo-2',4'-bismethoxycarbonyloxyacetophenone were boiled under reflux with 1.61 g (13.6 mmol) of N-acetylthiourea and 1.72 g (20.4 mmol) of NaHCO$_3$ in 45 ml of ethanol for 0.5 h. The reaction solution was cooled and admixed with 2.0 g (50 mmol) of NaOH in 20 ml of water. After stirring for 20 min at 0° C., the reaction solution was taken up with 30 ml of water and neutralized with semi-concentrated HCl. The resulting precipitate was filtered off and recrystallized from ethanol/water. 2.73 g of product were obtained. $^1$H NMR (DMSO-D$_6$): 12.20 (b, 1H), 10.85 (s, 1H), 9.46 (s, 1H), 7.64 (m, 1H), 7.38 (s, 1H), 6.28 (m, 2H), 2.15 (s, 3H) ppm; m.p. 264-264° C.

N-(4-(2,4-Dihydroxyphenyl)thiazol-2-yl)-4-(hydroxymethyl)cyclohexanecarboxamide

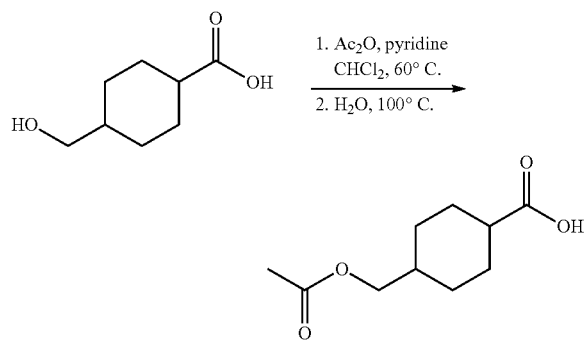

Procedure analogous to the literature.
BANYU Pharmaceutical Co. Ltd., EP2072519 A1, 2009 Yield: 96%. $^1$H NMR (DMSO-D$_6$): 12.03 (bs, 1H), 3.85, 3.82 (2×d, 2H), 2.50, 2.47 (2×m, 1H), 2.00 (s, 3H), 0.95-1.90 (m, 9H) ppm;

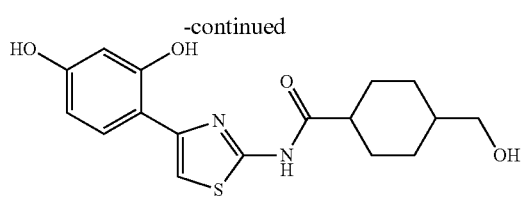

95 g (0.47 mol) of 4-acetoxymethylcyclohexanecarboxylic acid were heated under reflux in 350 ml of thionyl chloride for 2 h. After removing the excess thionyl chloride in vacuo, the residue was taken up in 1 l of toluene, and 71 g (0.94 mol) of thiourea were added. The reaction solution was boiled under reflux for 3 hours and then filtered off while hot. After cooling the mother liquor, the resulting white crystals were filtered off with suction, washed with toluene and dried in vacuo. Yield: 59 g. $^1$H NMR (DMSO-D$_6$): 11.03, 10.97 (2×s, 1H), 9.64 (bs, 1H), 9.35 (bs, 1H), 3.93, 3.82 (2×d, 2H), 2.61, 2.42 (2×m, 1H), 2.00 (s, 3H), 1.60 (m, 8H), 1.35, 0.94 (2×m, 1H) ppm;

79 g (228 mmol) of 2-bromo-2',4'-bismethoxycarbonyloxyacetophenone were boiled under reflux for 0.5 h with 59 g (228 mmol) of N-(4-acetoxymethylcyclohexylcarbonyl) thiourea and 29 g (340 mmol) of NaHCO$_3$ in 1000 ml of ethanol. The reaction solution was cooled and admixed with 73 g (1.8 mol) of NaOH in 300 ml of water. After stirring for 30 min at room temperature, the reaction solution was taken up with 300 ml of water and adjusted to pH=3 with 2N HCl. The resulting precipitate was filtered off and recrystallized from ethanol/water. 47 g of thiazol were obtained. $^1$H NMR (DMSO-D$_6$): 12.15, 12.10 (2×s, 1H), 10.96 (2×s, 1H), 9.47 (br, 2H), 7.64 (d, 1H), 7.39 (s, 1H), 6.29 (m, 2H), 4.40 (br, 1H), 3.32, 3.23 (2×d, 2H), 2.65, 2.44 (2×m, 1H), 1.90 (m, 1H), 1.78 (m, 2H), 1.50 (m, 5H), 0.94 (m, 1H) ppm; m.p. 152-160° C.

N-(4-(2,4-Dihydroxyphenyl)thiazol-2-yl)cyclohexanecarboxamide

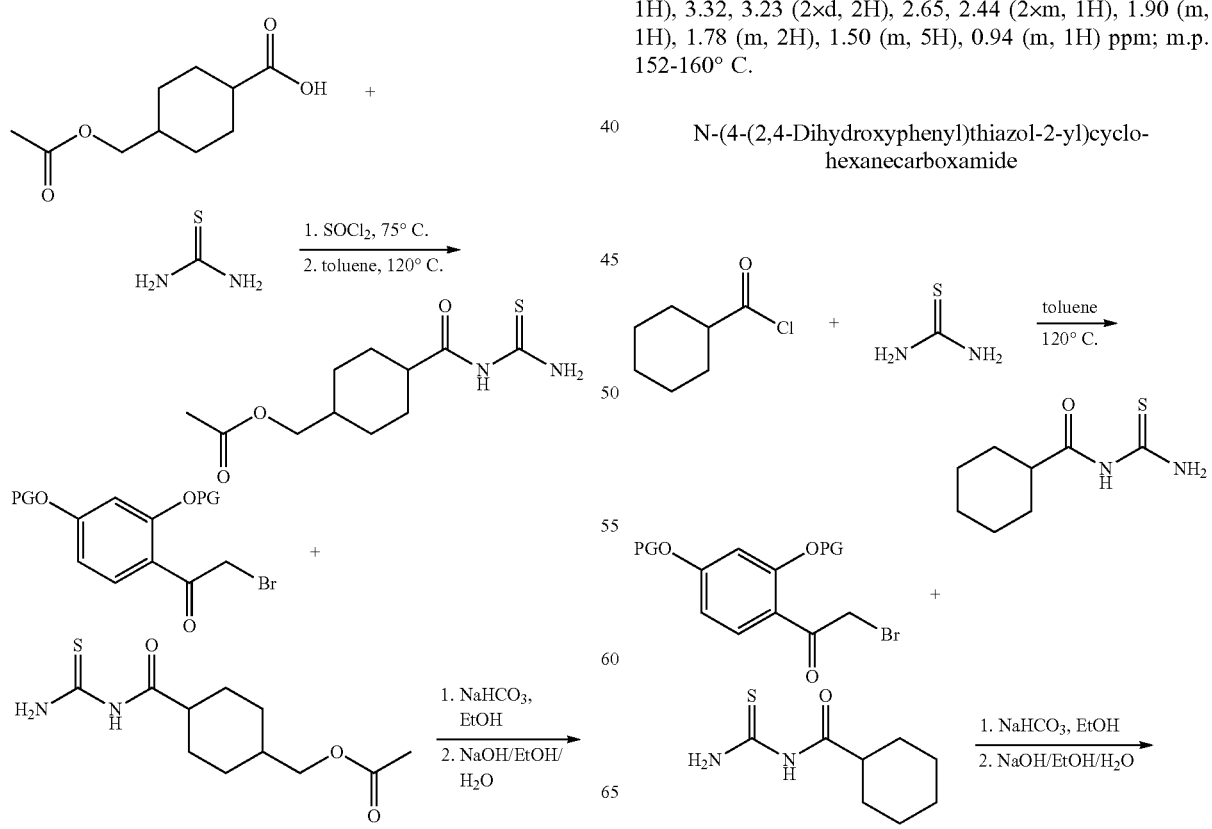

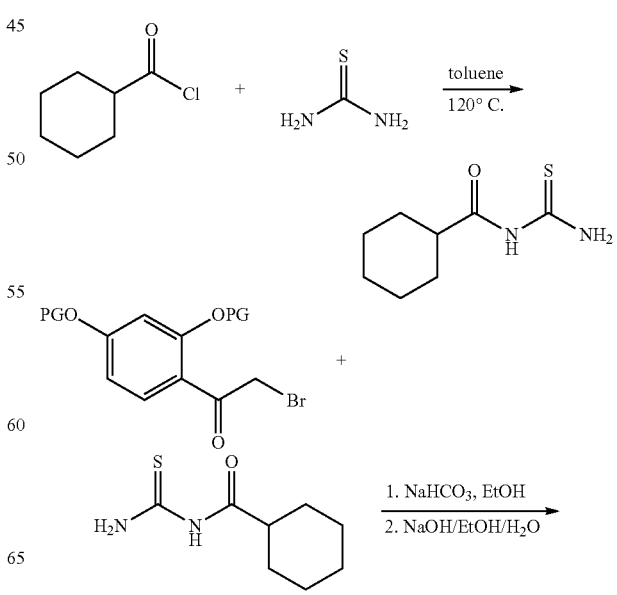

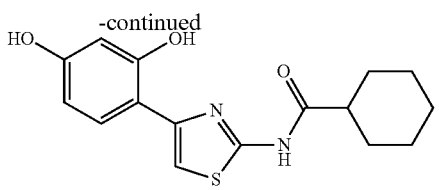

52 g (0.68 mol) of thiourea were introduced into toluene (500 ml), and 50 g (0.34 mol) of cyclohexanoyl chloride were added dropwise. The reaction solution was boiled under reflux for 3 hours, during which two phases formed. The upper phase was decanted off and cooled. The precipitated crystals were filtered off with suction, washed with toluene and recrystallized from methanol. Yield: 35 g. $^1$H NMR (DMSO-D$_6$): 10.98 (bs, 1H), 9.65 (bs, 1H), 9.32 (bs, 1H), 2.49 (t, 1H), 1.75 (m, 4H), 1.61 (m, 1H), 1.18 (m, 5H) ppm.

92 g (265 mmol) of 2-bromo-2',4'-bismethoxycarbonyloxyacetophenone were boiled under reflux for 0.5 h with 49.4 g (265 mmol) of N-cyclohexanoylthiourea and 34 g (397 mmol) of NaHCO$_3$ in 900 ml of ethanol. The reaction solution was cooled and admixed with 37 g (930 mmol) of NaOH in 300 ml of water. After stirring for 30 min at room temperature, the reaction solution was taken up with 300 ml of water and neutralized with 2N HCl. The ethanol was largely removed on a rotary evaporator. The precipitate formed was filtered off and recrystallized from ethanol/water. 70 g of thiazol were obtained. $^1$H NMR (DMSO-D$_6$): 12.14 (bs, 1H), 11.00 (bs, 1H), 9.48 (bs, 1H), 7.64 (1 arom. H), 7.39 (s, 1H), 6.30 (2 arom. H), 2.49 (m, 1H), 1.84 (m, 2H), 1.76 (m, 2H), 1.65 (m, 1H), 1.42 (m, 2H), 1.25 (m, 3H), ppm; m.p.: 262-266° C.

N-(4-(2,4-Dihydroxyphenyl)thiazol-2-yl)-2-(4-(hydroxymethyl)phenyl)acetamide

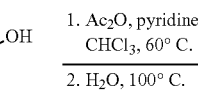

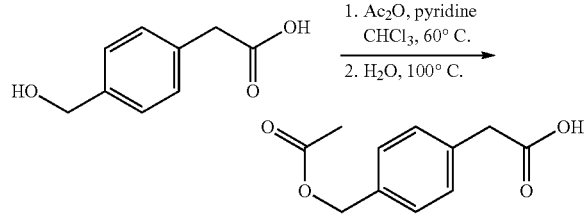

Procedure analogous to the literature.
BANYU Pharmaceutical Co. Ltd., EP2072519 A1, 2009
Yield: 76%. $^1$H NMR (DMSO-D$_6$): 12.31 (bs, 1H), 7.26 (m, 4H), 5.05 (s, 2H), 3.57 (s, 2H), 2.05 (s, 3H) ppm;

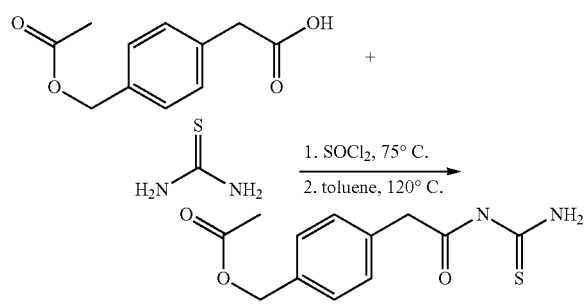

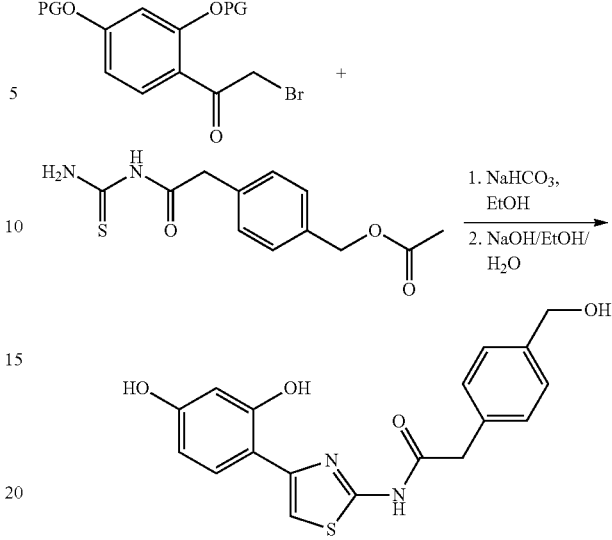

3.7 g (18 mmol) of 4-acetoxymethylphenylacetic acid were heated under reflux in 40 ml of thionyl chloride for 2 h. After removing the excess thionyl chloride in vacuo, the residue was taken up in 70 ml of toluene, and 2.7 g (36 mmol) of thiourea were added. The reaction solution was boiled under reflux for 3 hours and then the solvent was removed in vacuo. Purification was by means of column chromatography with cyclohexane/ethyl acetate 1/1 on silica gel. Yield: 2.7 g. $^1$H NMR (DMSO-D$_6$): 11.29 (bs, 1H), 9.55 (bs, 1H), 9.40 (bs, 1H), 7.30 (m, 4H), 5.04 (s, 2H), 3.71 (s, 2H), 2.05 (s, 3H) ppm;

3.5 g (10 mmol) of 2-bromo-2',4'-bismethoxycarbonyloxyacetophenone were boiled under reflux for 0.5 h with 2.7 g (10 mmol) of N-[2-(4-acetoxymethylphenyl)acetyl]thiourea and 1.3 g (15 mmol) of NaHCO$_3$ in 50 ml of ethanol. The reaction solution was cooled and admixed with 4.0 g (0.1 mol) of NaOH in 20 ml of water. After stirring for 2 h at 60° C., the reaction solution was taken up in 100 ml of water and adjusted to pH=3 with 2N HCl. The resulting precipitate was filtered off and recrystallized from ethanol/water. 1.3 g of thiazol were obtained. $^1$H NMR (DMSO-D$_6$): 12.44 (s, 1H), 10.80 (s, 1H), 9.48 (s, 1H), 7.66 (d, 1H), 7.41 (s, 1H), 7.29 (m, 4H), 6.32 (m, 2H), 5.13 (t, 1H), 4.47 (d, 2H), 3.77 (s, 2H) ppm; m.p. 254-256° C.

Cosmetic or dermatological preparations with a content of alkylamidothiazoles and their use for the treatment and/or prophylaxis of undesired skin pigmentation are likewise advantageous embodiments of the present invention.

It is particularly advantageous if such preparations comprise 0.000001 to 10% by weight, in particular 0.0001 to 3% by weight, very particularly 0.001 to 1% by weight, of one or more of the alkylamidothiazoles according to the invention, based on the total weight of the preparation.

Cosmetic and dermatological preparations according to the invention can be in various forms. Thus, they can be e.g. a solution, an anhydrous preparation, an emulsion or microemulsion of the water-in-oil (W/O) type or of the oil-in-water (O/W) type, a multiple emulsions, for example of the water-in-oil-in-water (W/O/W) type, a gel, a solid stick, a balm or else an aerosol. It is also advantageous according to the invention to administer the substances used according to the invention and/or their derivatives in encapsulated form, e.g. in collagen matrices and other customary encapsulation materials, e.g. as cellulose encapsulations, in gelatin or liposomally encapsulated.

It is also possible and advantageous within the context of the present invention to add the substances used according to the invention and/or their derivatives in aqueous systems or surfactant preparations for cleaning the skin and the hair.

The lipid phase can advantageously be selected from the following substance group:
mineral oils, mineral waxes
oils, such as triglycerides of capric acid or of caprylic acid, also natural oils such as e.g. castor oil;
fats, waxes and other natural and synthetic fatty bodies, preferably esters of fatty acids with alcohols of low carbon number, e.g. with isopropanol, propylene glycol or glycerol, or esters of fatty alcohols with alkanoic acids of low carbon number or with fatty acids;
alkyl benzoates;
silicone oils such as dimethylpolysiloxanes, diethylpolysiloxanes, diphenylpolysiloxanes and mixtures thereof.

The oil phase of the emulsions, oleogels or hydrodispersions or lipodispersions within the context of the present invention is advantageously selected from the group of esters of saturated and/or unsaturated, branched and/or unbranched alkanecarboxylic acids of chain length from 3 to 30 carbon atoms and saturated and/or unsaturated, branched and/or unbranched alcohols of chain length from 3 to 30 carbon atoms, from the group of esters of aromatic carboxylic acids and saturated and/or unsaturated, branched and/or unbranched alcohols of chain length from 3 to 30 carbon atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In particular, mixtures of the aforementioned solvents are used. In the case of alcohol solvents, water may be a further constituent.

Emulsions according to the invention are advantageous and comprise e.g. said fats, oils, waxes and other fatty bodies, and also water and an emulsifier, as is usually used for such a type of formulation.

Suitable propellants for preparations according to the invention which can be sprayed from aerosol containers are the customary known readily volatile, liquefied propellants, for example hydrocarbons (propane, butane, isobutene), which can be used on their own or in a mixture with one another. Compressed air can also advantageously be used.

The examples below are intended to illustrate the present invention without limiting it. Unless stated otherwise, all of the quantities, fractions and percentages given are percentages by weight, based on the weight and the total amount or on the total weight of the preparations.

Formulation Examples

| INCI/Substance | Formula 1 | Formula 2 | Formula 3 | Formula 4 | Formula 5 | Formula 6 |
|---|---|---|---|---|---|---|
| N-(4-(2,4-Dihydroxyphenyl)-thiazol-2-yl)isobutyramide | 0.10 | | | | | |
| 4-(2-Isopropylamino)thiazol-4-yl)benzene-1,3-diol | | 0.10 | | | | |
| 4-(2-tert-Butylamino)thiazol-4-yl)benzene-1,3-diol | | | 0.10 | | | |
| N-(4-(2,4-Dihydroxyphenyl)-thiazol-2-yl)pivalamide | | | | 0.10 | | |
| N-(4-(2,4-Dihydroxyphenyl)-thiazol-2-yl)butyramide | | | | | 0.10 | |
| 4-(2-Propylamino)thiazol-4-yl)benzene-1,3-diol | | | | | | 0.10 |
| Behenyl alcohol | 1.20 | 1.20 | 1.20 | 1.20 | 1.20 | 1.20 |
| Cetyl alcohol | 2.00 | 2.00 | 2.00 | 2.00 | 2.00 | 2.00 |
| Caprylic/capric triglyceride | 2.50 | 2.50 | 2.50 | 2.50 | 2.50 | 2.50 |
| Dicaprylyl carbonate | 2.50 | 2.50 | 2.50 | 2.50 | 2.50 | 2.50 |
| Dimethicone | 0.35 | 0.35 | 0.35 | 0.35 | 0.35 | 0.35 |
| C12-15 Alkyl benzoate | 2.50 | 2.50 | 2.50 | 2.50 | 2.50 | 2.50 |
| Cyclomethicone | 2.15 | 2.15 | 2.15 | 2.15 | 2.15 | 2.15 |
| Glyceryl stearate citrate | 2.00 | 2.00 | 2.00 | 2.00 | 2.00 | 2.00 |
| Glycerin | 8.70 | 8.70 | 8.70 | 8.70 | 8.70 | 8.70 |
| Butylene glycol | 3.00 | 3.00 | 3.00 | 3.00 | 3.00 | 3.00 |
| Water + sodium hydroxide | 0.03 | 0.03 | 0.03 | 0.03 | 0.03 | 0.03 |
| Methylparaben | 0.20 | 0.20 | 0.20 | 0.20 | 0.20 | 0.20 |
| Propylparaben | 0.10 | 0.10 | 0.10 | 0.10 | 0.10 | 0.10 |
| Phenoxyethanol | 0.40 | 0.40 | 0.40 | 0.40 | 0.40 | 0.40 |
| Carbomer | 0.10 | 0.10 | 0.10 | 0.10 | 0.10 | 0.10 |
| Sodium polyacrylate | 0.20 | 0.20 | 0.20 | 0.20 | 0.20 | 0.20 |
| Water | ad 100.00 | | | | | |

| INCI/Substance | Formula 7 | Formula 8 | Formula 9 | Formula 10 |
|---|---|---|---|---|
| N-(4-(2,4-Dihydroxyphenyl)-thiazol-2-yl)cyclohexane-carboxamide | 0.10 | | | |
| 4-(2-(Cyclohexylamino)thiazol-4-yl)benzene-1,3-diol | | 0.10 | | |
| N-(4-(2,4-Dihydroxyphenyl)-thiazol-2-yl)heptanamide | | | 0.10 | |
| 4-(2-(Hexylamino)thiazol-4-yl)benzene-1,3-diol | | | | 0.10 |

| | | | | |
|---|---|---|---|---|
| -continued | | | | |
| Behenyl alcohol | 1.20 | 1.20 | 1.20 | 1.20 |
| Cetyl alcohol | 2.00 | 2.00 | 2.00 | 2.00 |
| Caprylic/capric triglyceride | 2.50 | 2.50 | 2.50 | 2.50 |
| Dicaprylyl carbonate | 2.50 | 2.50 | 2.50 | 2.50 |
| Dimethicone | 0.35 | 0.35 | 0.35 | 0.35 |
| C12-15 Alkyl benzoate | 2.50 | 2.50 | 2.50 | 2.50 |
| Cyclomethicone | 2.15 | 2.15 | 2.15 | 2.15 |
| Glyceryl stearate citrate | 2.00 | 2.00 | 2.00 | 2.00 |
| Glycerin | 8.70 | 8.70 | 8.70 | 8.70 |
| Butylene glycol | 3.00 | 3.00 | 3.00 | 3.00 |
| Water + sodium hydroxide | 0.03 | 0.03 | 0.03 | 0.03 |
| Methylparaben | 0.20 | 0.20 | 0.20 | 0.20 |
| Propylparaben | 0.10 | 0.10 | 0.10 | 0.10 |
| Phenoxyethanol | 0.40 | 0.40 | 0.40 | 0.40 |
| Carbomer | 0.10 | 0.10 | 0.10 | 0.10 |
| Sodium polyacrylate | 0.20 | 0.20 | 0.20 | 0.20 |
| Water | ad 100.00 | | | |

The invention claimed is:

1. An alkylamidothiazole selected from the group consisting of

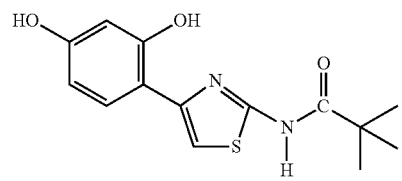

N-(4-(2,4-dihydroxyphenyl)thiazol-2-yl)pivalamide,

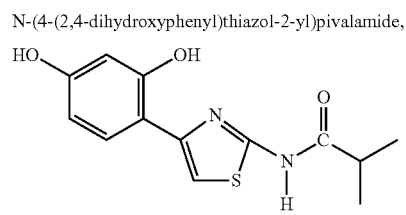

N-(4-(2,4-dihydroxyphenyl)thiazol-2-yl)isobutyramide,

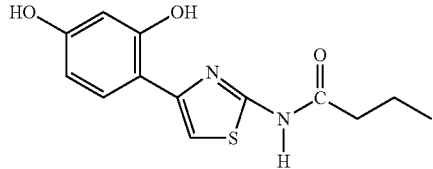

N-(4-(2,4-dihydroxyphenyl)thiazol-2-yl)butyramide,

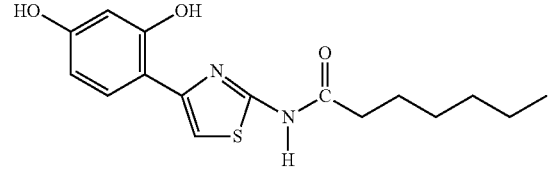

N-(4-(2,4-dihydroxyphenyl)thiazol-2-yl)heptanamide,

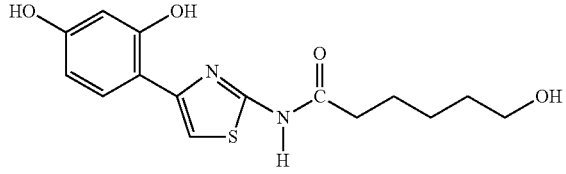

N-(4-(2,4-dihydroxyphenyl)thiazol-2-yl)-6-hydroxyhexanamide,

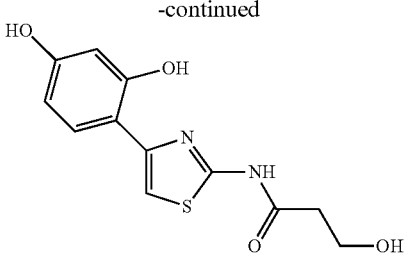

N-(4-(2,4-dihydroxyphenyl)thiazol-2-yl)-3-hydroxypropanamide,

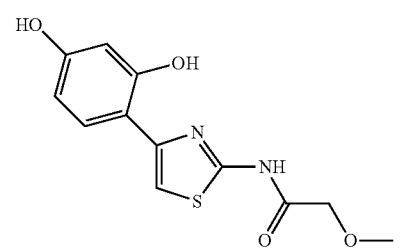

N-(4-(2,4-dihydroxyphenyl)thiazol-2-yl)-2-methoxyacetamide,

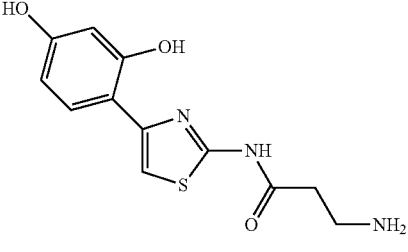

3-amino-N-(4-(2,4-dihydroxyphenyl)thiazol-2-yl)propanamide,

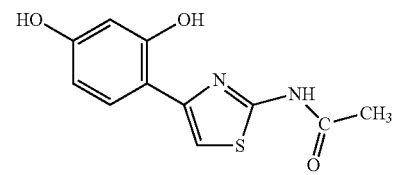

N-(4-(2,4-dihydroxyphenyl)thiazol-2-yl)acetamide,

-continued

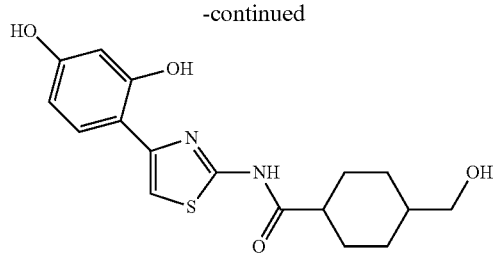

N-(4-(2,4-dihydroxyphenyl)thiazol-2-yl)-4-(hydroxymethyl)cyclohexanecarboxamide,

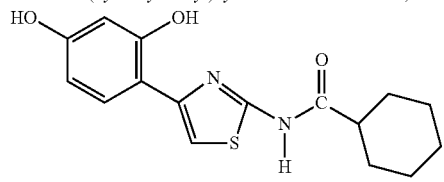

N-(4-(2,4-dihydroxyphenyl)thiazol-2-yl)cyclohexanecarboxamide, and

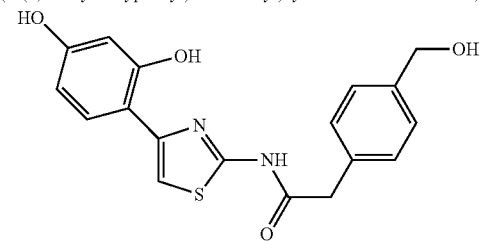

N-(4-(2,4-dihydroxyphenyl)thiazol-2-yl)-2-(4-(hydroxymethyl)phenyl)acetamide, either as a free base or a cosmetically and dermatologically acceptable salt thereof.

2. An alkylamidothiazole of claim 1, wherein the alkylamidothiazole is present as a salt in the form of a halide, carbonate, ascorbate, sulfate, acetate or phosphate.

3. An alkylamidothiazole of claim 1, namely N-(4-(2,4-dihydroxyphenyl)thiazol-2-yl)isobutyramide.

4. An alkylamidothiazole of claim 1, namely N-(4-(2,4-dihydroxyphenyl)thiazol-2-yl)butyramide.

5. An alkylamidothiazole of claim 1, namely N-(4-(2,4-dihydroxyphenyl)thiazol-2-yl)pivalamide.

6. An alkylamidothiazole of claim 1, namely N-(4-(2,4-dihydroxyphenyl)thiazol-2-yl)cyclohexanecarboxamide.

7. An alkylamidothiazole of claim 1, namely N-(4-(2,4-dihydroxyphenyl)thiazol-2-yl)-4-(hydroxymethyl)cyclohexanecarboxamide.

8. An alkylamidothiazole of claim 1, namely N-(4-(2,4-dihydroxyphenyl)thiazol-2-yl)-2-(4-hydroxymethyl)phenyl)acetamide.

9. A cosmetic or dermatological composition, wherein the composition comprises at least one alkylamidothiazole of claim 1 and a cosmetic or dermatological carrier.

10. The composition of claim 9, wherein the composition comprises from 0.000001% to 10% by weight of the at least one alkylamidothiazole, based on a total weight of the preparation.

11. The composition of claim 10, wherein the composition comprises from 0.0001% to 3% by weight of the at least one alkylamidothiazole.

12. The composition of claim 10, wherein the composition comprises from 0.001% to 1% by weight of the at least one alkylamidothiazole.

13. The composition of claim 9, wherein the composition comprises at east N-(4-(2,4-dihydroxyphenyl)thiazol-2-yl) isobutyramide.

14. The composition of claim 10, wherein the composition comprises at least N-(4-(2,4-dihydroxyphenyl)thiazol-2-yl)isobutyramide.

15. The composition of claim 11, wherein the composition comprises at least N-(4-(2,4-dihydroxyphenyl)thiazol-2-yl) isobutyramide.

16. The composition of claim 12, wherein the composition comprises at least N-(4-(2,4-dihydroxyphenyl)thiazol-2-yl)isobutyramide.

17. A method for the cosmetic or dermatological treatment of undesired skin pigmentation in a subject in need thereof, wherein the method comprises applying to skin affected by the undesired skin pigmentation the composition of claim 9 in an amount which is sufficient to treat the undesired skin pigmentation.

18. A method for the prophylaxis of undesired skin pigmentation, wherein the method comprises applying to skin the composition of claim 9 in an amount which is sufficient to prevent undesired skin pigmentation.

19. The method of claim 17, wherein the composition comprises at least N-(4-(2,4-dihydroxyphenyl)thiazol-2-yl) isobutyramide.

20. The method of claim 18, wherein the composition comprises at least N-(4-(2,4-dihydroxyphenyl)thiazol-2-yl) isobutyramide.

* * * * *